(12) United States Patent
Melsheimer et al.

(10) Patent No.: US 8,256,949 B2
(45) Date of Patent: Sep. 4, 2012

(54) APPARATUS AND METHOD FOR MIXING AND DISPENSING A BONE CEMENT MIXTURE

(75) Inventors: Jeffry S. Melsheimer, Springville, IN (US); Jonathan Lee Bennett, Bloomington, IN (US); Jessica L. Burke, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 835 days.

(21) Appl. No.: 12/343,964

(22) Filed: Dec. 24, 2008

(65) Prior Publication Data
US 2009/0171361 A1    Jul. 2, 2009

Related U.S. Application Data

(60) Provisional application No. 61/017,065, filed on Dec. 27, 2007.

(51) Int. Cl.
*B01F 7/16* (2006.01)
*A61B 17/56* (2006.01)

(52) U.S. Cl. ............ 366/130; 222/246; 366/182.1; 366/189; 606/93

(58) Field of Classification Search .......... 366/182, 366/182.1, 130, 139, 150.1, 182.3, 189; 222/82, 222/246; 206/222; 606/92–94
See application file for complete search history.

(56) References Cited

U.S. PATENT DOCUMENTS

| | | | | |
|---|---|---|---|---|
| 3,144,966 A | * | 8/1964 | Cook | 222/136 |
| 3,349,966 A | * | 10/1967 | Schwartzman | 222/80 |
| 3,425,598 A | * | 2/1969 | Kobernick | 222/83 |
| 3,595,439 A | | 7/1971 | Newby | |
| 3,724,460 A | * | 4/1973 | Gomez et al. | 604/88 |
| 3,739,947 A | * | 6/1973 | Baumann et al. | 222/136 |
| 3,762,540 A | * | 10/1973 | Baumann et al. | 206/219 |
| 4,014,330 A | * | 3/1977 | Genese | 604/88 |
| 4,060,082 A | * | 11/1977 | Lindberg et al. | 604/89 |
| 4,171,698 A | * | 10/1979 | Genese | 604/88 |
| 4,304,869 A | * | 12/1981 | Dyke | 435/287.6 |
| 4,306,554 A | * | 12/1981 | Schwartz et al. | 604/87 |
| 4,453,934 A | * | 6/1984 | Gahwiler et al. | 604/191 |
| 4,461,837 A | * | 7/1984 | Karle et al. | 435/287.4 |
| 4,512,768 A | * | 4/1985 | Rangaswamy | 604/191 |
| 4,556,325 A | | 12/1985 | Katzin | |
| 4,648,532 A | * | 3/1987 | Green | 222/82 |
| 4,676,655 A | * | 6/1987 | Handler | 366/130 |
| 4,713,062 A | * | 12/1987 | Stevanato | 604/203 |
| 4,792,329 A | * | 12/1988 | Schreuder | 604/90 |
| 4,941,751 A | * | 7/1990 | Muhlbauer | 366/182.1 |
| 4,968,302 A | * | 11/1990 | Schluter et al. | 604/135 |

(Continued)

*Primary Examiner* — Yogendra Gupta
*Assistant Examiner* — Emmanuel S Luk
(74) *Attorney, Agent, or Firm* — Woodard, Emhardt, Moriarty, McNett & Henry LLP (57) ABSTRACT

Among other things, an apparatus for mixing and dispensing a bone cement mixture are provided. In certain embodiments, the apparatus includes a housing having a first chamber for containing an ampoule having a first bone cement component. The housing has a second chamber for containing a second bone cement component and the first and second chambers are in fluid communication. An ampoule breaking device is disposed within the first chamber and is configured to engage and break the ampoule for release of the first bone cement component. Disposed within the second chamber is an impeller that is configured to rotate such that the impeller mixes the first and second bone cement components together to form the bone cement mixture. Adjacent the impeller is a displacer that is configured to advance through the second chamber, receiving the impeller and dispensing the bone cement mixture.

20 Claims, 7 Drawing Sheets

U.S. PATENT DOCUMENTS

| | | | | |
|---|---|---|---|---|
| 5,193,907 | A | 3/1993 | Faccioli et al. | |
| 5,392,904 | A * | 2/1995 | Frick et al. | 206/219 |
| 5,429,603 | A * | 7/1995 | Morris | 604/88 |
| 5,435,645 | A | 7/1995 | Faccioli et al. | |
| 5,443,182 | A | 8/1995 | Tanaka et al. | |
| RE35,276 | E * | 6/1996 | Chan | 366/139 |
| 5,549,380 | A | 8/1996 | Lidgren et al. | |
| 5,695,472 | A * | 12/1997 | Wyrick | 604/136 |
| 5,934,803 | A | 8/1999 | Hutter | |
| 6,024,480 | A * | 2/2000 | Seaton et al. | 366/130 |
| 6,042,262 | A | 3/2000 | Hajianpour | |
| 6,116,773 | A | 9/2000 | Murray | |
| 6,176,607 | B1 | 1/2001 | Hajianpour | |
| 6,309,372 | B1 * | 10/2001 | Fischer et al. | 604/82 |
| 6,312,149 | B1 | 11/2001 | Sjovall et al. | |
| 6,343,718 | B1 * | 2/2002 | Montenieri et al. | 222/326 |
| 6,516,977 | B2 | 2/2003 | Chan | |
| 6,656,150 | B2 * | 12/2003 | Hill et al. | 604/89 |
| 6,682,347 | B2 * | 1/2004 | Aoyagi et al. | 433/90 |
| 6,796,701 | B2 | 9/2004 | Wahlig et al. | |
| 6,869,284 | B2 * | 3/2005 | Aoyagi et al. | 433/90 |
| 6,953,445 | B2 * | 10/2005 | Wilmot et al. | 604/89 |
| 6,984,063 | B2 | 1/2006 | Barker et al. | |
| 7,029,163 | B2 | 4/2006 | Barker et al. | |
| 7,073,936 | B1 | 7/2006 | Jonsson | |
| 7,112,205 | B2 * | 9/2006 | Carrison | 606/92 |
| 7,216,761 | B2 | 5/2007 | deVries | |
| 7,311,195 | B2 * | 12/2007 | Schmid | 206/219 |
| 7,497,355 | B2 * | 3/2009 | Horner et al. | 222/137 |
| 7,506,783 | B2 * | 3/2009 | Brennan et al. | 222/137 |
| 7,556,614 | B2 * | 7/2009 | Griffiths et al. | 604/89 |
| 7,748,567 | B2 * | 7/2010 | Horner et al. | 222/135 |
| 7,806,297 | B2 * | 10/2010 | Pauser et al. | 222/129 |
| 2001/0020155 | A1 * | 9/2001 | Mikkelsen et al. | 604/187 |
| 2006/0028907 | A1 | 2/2006 | Barker et al. | |
| 2006/0164913 | A1 | 7/2006 | Arramon | |
| 2006/0203608 | A1 | 9/2006 | Barker et al. | |
| 2006/0227653 | A1 | 10/2006 | Keller | |
| 2006/0274601 | A1 | 12/2006 | Seaton, Jr. | |
| 2008/0195082 | A1 * | 8/2008 | Pauser et al. | 604/518 |

* cited by examiner

APPARATUS AND METHOD FOR MIXING AND DISPENSING A BONE CEMENT MIXTURE

The present disclosure relates to an apparatus, a kit and a method for mixing and dispensing a bone cement mixture. The benefit of U.S. Provisional Application Ser. No. 61/017,065 (filed on Dec. 27, 2007) is claimed, and U.S. Provisional Application Ser. No. 61/017,065 is incorporated herein by reference.

BACKGROUND

There is a clinical need to fill and stabilize damaged bones of patients, such as for example, filling defects in collapsed vertebra of patients suffering from severe back pain caused by osteoporosis, metastatic tumors or back injuries. Currently, these defects are repaired using multi-component bone cements that are mixed in open containers, transferred to a device and injected into the damaged bone where the mixture chemically reacts or cures to form a solid support structure.

Most widely used bone cements are based on polymethylmethacrylate (PMMA) and hydroxylapatite. These materials have relatively good strength characteristics, but have a number of drawbacks. These cements are a two-part chemically reactive system and have approximately five to ten minutes of working time once the components are mixed. As for example with the PMMA based system, one of the components is a liquid monomer methylmethacrylate (MMA), which is noxious and toxic to handle. The other component, the polymer component (PMMA), is a powder that can be difficult to mix thoroughly. Moreover, current methods of mixing these two components together are typically done by hand in an open container or dish. This procedure permits significant vaporization of the noxious liquid monomer MMA. Also, the working time increases between mixing and dispensing because once the mixture is mixed it then needs to be transferred to a syringe for injection into the damaged bone. Moreover, the working time is limited because the viscosity of the cement constantly increases during mixing, thus making transferring of the mixture to the syringe and injection of the mixture into the damaged bone more difficult. Often, a very high injection pressure and/or large bore needles may be necessary to inject the mixture, especially if it's near the end of the cement's working life.

SUMMARY

Embodiments of the present disclosure provide an apparatus, a kit and a method that facilitates mixing and dispensing the bone cement mixture such that the interventionalist and the patient have minimal exposure to the noxious vapors of the monomer, as well as providing more flexible working time for suitable injectionability of the mixture into the damaged bone. In at least some examples of the present disclosure, the bone cement components are pre-measured and contained within the apparatus, which may eliminate the possibility of spilling the bone cement components and minimize handling during preparation of the bone cement mixture.

In at least one embodiment of the present disclosure, an apparatus for mixing and dispensing a bone cement mixture is provided. The apparatus comprises a housing having a longitudinal axis. The housing has a first chamber formed therein that is for containing an ampoule having a first bone cement component. The housing has a second chamber formed therein for containing a second bone cement component and the first and second chambers are in fluid communication. The housing includes an outlet in fluid communication with the second chamber. Through the outlet, the bone cement mixture is dispensed from the apparatus. An ampoule breaking device is disposed within the first chamber and is configured to engage the ampoule to break the ampoule for release of the first bone cement component into the first chamber. Disposed within the second chamber is an impeller that is configured to rotate about the longitudinal axis such that the impeller mixes the first and second bone cement components together to form the bone cement mixture. Adjacent the impeller is a displacer that is configured to advance through the second chamber, receiving the impeller and advancing the bone cement mixture from the second chamber through the outlet.

In at least one other embodiment of the present disclosure, a bone cement substitute kit for mixing a bone cement mixture and dispensing the bone cement mixture into a damaged bone of a patient is provided. The kit comprises an ampoule having a first bone cement component disposed therein and a second bone cement component. An apparatus including a housing having a longitudinal axis. The housing has a first chamber formed therein that is for containing the ampoule. The housing has a second chamber formed therein for containing the second bone cement component and the first and second chambers are in fluid communication. The housing includes an outlet in fluid communication with the second chamber. Through the outlet, the bone cement mixture is dispensed from the apparatus. An ampoule breaking device is disposed within the first chamber and is configured to engage the ampoule to break the ampoule for release of the first bone cement component into the first chamber. Disposed within the second chamber is an impeller that is configured to rotate about the longitudinal axis such that the impeller mixes the first and second bone cement components together to form the bone cement mixture. Adjacent the impeller is a displacer that is configured to advance through the second chamber, receiving the impeller and advancing the bone cement mixture from the second chamber through the outlet. The kit further comprises a needle in fluid communication with the outlet that is configured for receiving the bone cement mixture from the apparatus and for advancing the bone cement mixture into the damaged bone of the patient.

In at least another embodiment of the present disclosure, a method for mixing a bone cement mixture and for dispensing the bone cement mixture into the damaged bone of a patient is provided. The method comprises providing an apparatus having a longitudinal axis, a first chamber and a second chamber in fluid communication with the first chamber. In fluid communication with the second chamber is an outlet. Disposed within the first chamber is an ampoule breaking device. An impeller is disposed within the second chamber and a displacer is disposed adjacent to the impeller. A first bone cement component is released into the first chamber by breaking the ampoule within the first chamber with the ampoule breaking device. The first bone cement component is advanced from the first chamber to the second chamber which contains a second bone cement component. By rotating the impeller about the longitudinal axis, the first and second bone cement components are mixed to form the bone cement mixture. Into the damaged bone of a patient, a needle in fluid communication with the outlet is inserted. The bone cement mixture is dispensed from the apparatus into the damaged bone of the patient via the needle by advancing the displacer through the second chamber. The displacer receives the impeller and advances the bone cement mixture from the second chamber through the outlet. The bone cement mixture is cured, which sets and hardens the bone cement mixture to stabilize the damage bone of the patient.

Further objects, features and advantages of the disclosure will become apparent from consideration of the following description and the appended claims when taken in connection with the accompanying drawings.

DETAILED DESCRIPTION OF THE DISCLOSURE

Detailed embodiments of the present disclosure are disclosed herein. It is understood however, that the disclosed embodiments are merely exemplary of the disclosure and may be embodied in various and alternative forms. The figures are not necessarily to scale; some figures may be configured to show the details of a particular component. Therefore, specific structural and functional details disclosed herein are not to be interpreted as limiting but merely as a representative basis with the claims and for teaching one skilled in the art to practice the present disclosure.

Examples of the present disclosure seek to overcome some of the concerns associated with stabilizing and/or repairing the damaged bone of a patient with bone cement while minimizing toxic effects to both the patient and the interventionalist, as well as enhancing the ease of handling for both mixing and introducing the bone cement into the damaged bone.

Employing the principles of the present disclosure is, for example, an apparatus, a kit and a method for stabilizing and/or repairing a damaged bone of a patient. The apparatus, which is utilized in both the kit and the method, is a closed mixing and dispensing system having two chambers that are in fluid communication with one another. Each chamber is initially for containing one of the components of a two component bone cement system. For example, an ampoule containing the first bone cement component may be contained in the first chamber. The apparatus is configured such that the first bone cement component can be released from the ampoule into the first chamber where it may be further advanced into the second chamber, which contains the second bone cement component. In one aspect, a valve may be actuated to selectively open and close fluid communication between the first and second chambers where in the open position, the first bone cement mixture may be advanced into the second chamber. Within the second chamber, an impeller mixes the first bone cement component with the second bone cement component to form a bone cement mixture. A displacer advances through the second chamber, receiving the impeller and advancing the bone cement mixture from the second chamber through an outlet and into a damaged bone of a patient via a needle in fluid communication with the outlet. The apparatus preferably mixes the bone cement components together without releasing noxious monomer fumes (i.e. in a closed or substantially closed system) contained in at least one of the bone cement components. Moreover, since the apparatus is configured to dispense the bone cement mixture, there is no need for transferring the mixture from another source into the apparatus, or from the apparatus to another dispenser. Furthermore, in at least one example, the bone cement components are pre-measured and sealably packaged within the apparatus, which preferably eliminates measuring errors and spilling of the contents during handling. Accordingly, the apparatus minimizes the mixing and dispensing time of the bone cement and thus, enhances the remaining working time for introducing the mixture into the damaged bone. Once the bone cement mixture is introduced into the damaged bone of the patient it cures to form a solid structure which stabilizes the bone.

Figure 1:
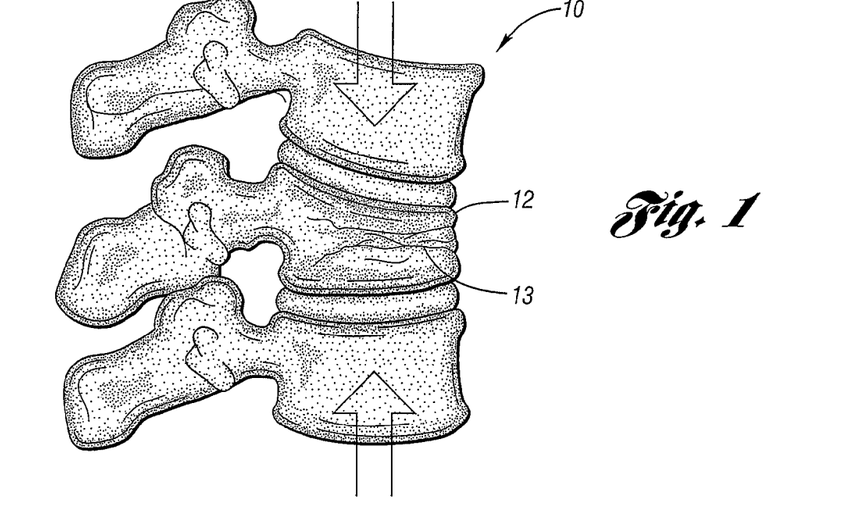
FIG. 1 is a perspective view of a collapsed vertebra.

Referring now to the drawings, FIG. 1 illustrates a vertebra 10 which includes a collapsed vertebra 12 with a compression fracture 13. The vertebra 10 may be for example in the thoracic or lower spine of the patient. In the compression fracture 13 of the vertebra 12, the bone tissue of the vertebral body collapses. This condition is commonly caused by osteoporosis and less often by a tumor, or trauma to the back.

Figure 2:
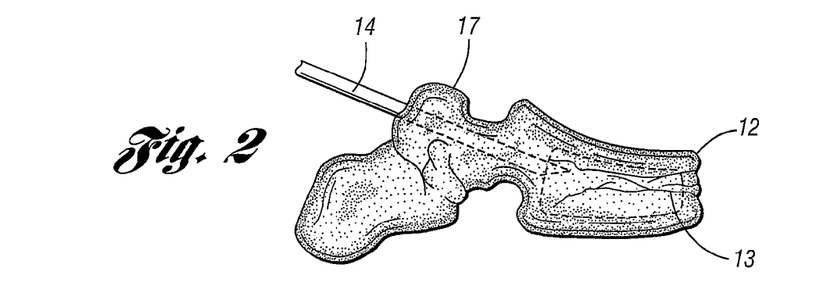
FIG. 2 is a partial side view of a device for stabilizing a collapsed vertebra in accordance with one embodiment of the present disclosure.
Figure 3:
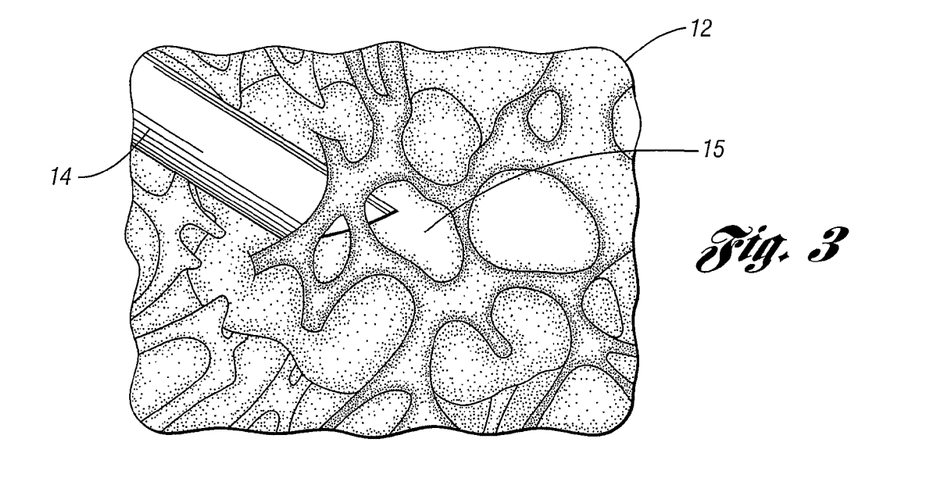
FIG. 3 is an enlarged view of FIG. 2.

Referring now to FIGS. 2 and 3, at least one embodiment of the present disclosure is provided. The collapsed vertebra 12 may be stabilized by either vertebroplasty or kyphoplasty, both of which are medical procedures for restoring the structural integrity of the collapsed vertebra 12. These procedures stabilize the collapsed vertebra 12 by filling in open spaces 15 within the vertebra 12 to provide a more continuous and solid form. Kyphoplasty may further stabilize the vertebra 12 by restoring vertebral spacing which alleviates nerve pinching from the vertebra 12. It should be noted that the present disclosure applies to both of these medical procedures and other procedures for stabilizing and/or repairing the damaged bone of patients despite many of the various embodiments discussed herein as describing using vertebroplasty.

Vertebroplasty involves that the patient remain laying throughout the entire procedure. It is performed under local anesthesia and/or a light sedative. A small nick is then made in the skin near the spine and a needle 14 is inserted percutaneously. As illustrated in FIG. 3, the needle 14 may be inserted into the interior open spaces 15 of the vertebra 12, for example via or through the left or right pedicle 17 of the vertebra 12.

Figure 4:
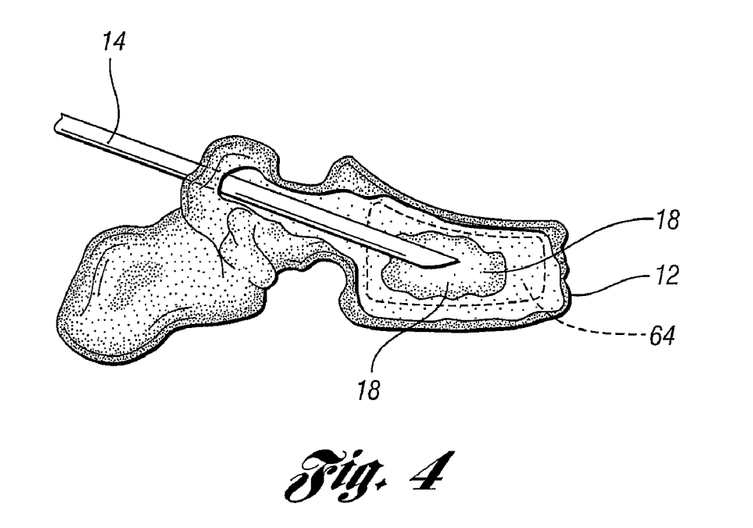
FIG. 4 is a partial side view of a device for stabilizing a collapsed vertebra in accordance with yet another embodiment of the present disclosure.
Figure 5:
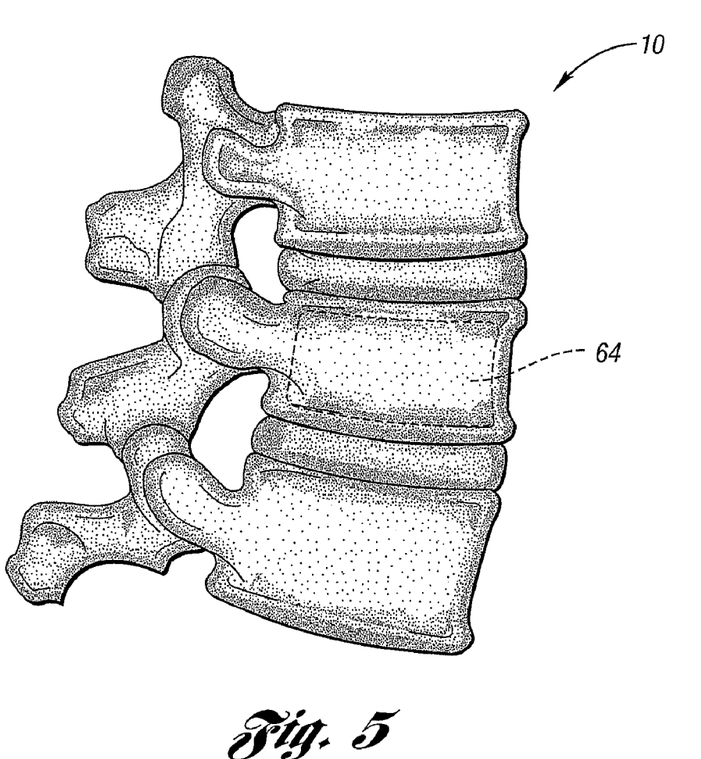
FIG. 5 is a partial side view of a stabilized collapsed vertebra in accordance with one example of the present disclosure.

Referring to FIGS. 4 and 5, the bone cement mixture 18 may be dispensed from an apparatus (not shown) through the needle 14 and into the vertebra 12 to form a solid structure 64 that supports the collapsed vertebra 12. The bone cement mixture 18 forms a solid structure 64 by chemically reacting or curing to become a solid. The stabilizing structure 64 may be formed within the collapsed vertebra 12 and may help restore vertebral spacing and alleviate nerve pinching by supporting the collapsed vertebra 12 generally in at least a compressive mode. Preferably, the structure 64 substantially fills in the open space 15 of the collapsed vertebra 12 providing a more dense and continuous vertebra 12 which enhances the mobility and relieves the pain of the patient.

Figure 11:
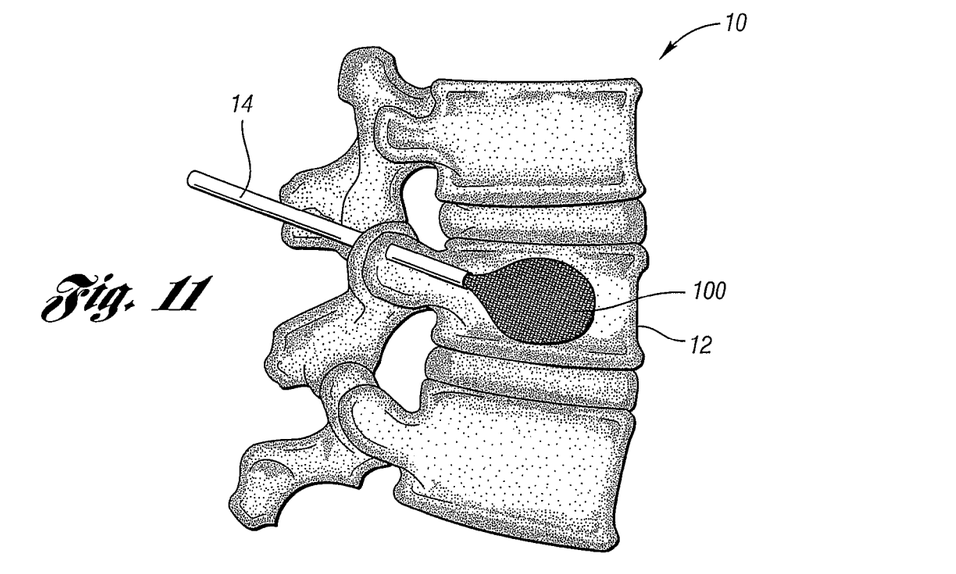
FIG. 11 is a partial side view of a device for stabilizing a collapsed vertebra in accordance with another embodiment of the present disclosure.

Referring to FIG. 11, at least one other embodiment for stabilizing a collapsed vertebra 12 of a patient is provided. The procedure includes placing a balloon 100 into the collapsed vertebra 12. The balloon 100 may be positioned in the vertebra 12 for example via the needle 14, a catheter or mandrel. The balloon 100 is then filled with the bone cement mixture 18 and sealed. The balloon 100 may be sealed for example by twisting the needle 14 and shearing the corresponding end portion of the balloon 100 or alternatively by applying any suitable adhesive, such as a cyanoacrylate, to the end portion. The bone cement mixture 18 within the sealed balloon 100 cures to form the solid support structure 64 within the collapsed vertebra 12.

The balloon 100 may be made of any suitable material used for medical intracorporeal balloon devices. However, a polymer impermeable to body fluids and PMMA may be preferred. An example of such material is polyethylene terephthalate (PET) or polybutylene terephthalate (PBT).

Referring to FIGS. 6-9b, at least one embodiment of an apparatus for mixing a bone cement mixture and for dispensing the bone cement mixture is provided. The apparatus 20 comprises a housing 22 having a longitudinal axis 24. In one example, the housing 22 has a substantially cylindrical shape disposed along the longitudinal axis.

The housing 22 has a first chamber 26 that is formed therein. The first chamber 26 is for containing an ampoule 28 having a first bone cement component 30 (shown in FIG. 12) disposed therein. In at least one example, the ampoule 28 is made of glass which is sealed (e.g. single-piece or multiple-pieces without openings) and contains a liquid monomer bone cement component 30 such as MMA. The ampoule 28 may be made of other suitable materials which are chemically compatible with bone cement components and which may also be broken when a force is applied to the ampoule 28 to release the first bone cement component 30 from the ampoule 28 and into the first chamber 26. As seen in the example of FIG. 6, a cap 31 is connected to housing 22 to enclose and seal chamber 26, to prevent or limit escape of cement component 30 or fumes from it.

A second chamber 32 is formed within the housing 22. The second chamber 32 is for containing a second bone cement component 34 (shown in FIG. 12). The second chamber 32 is in fluid communication with the first chamber 26. In at least one example, the first chamber is positioned above the second chamber and a port 36 provides fluid communication between the first and second chambers 26 and 32. Cement component 34 may be pre-loaded into chamber 32 (e.g. prior to inserting ampoule 28 into chamber 26). For example, component 34 can be placed in chamber 26 to move through port 36 and into chamber 32. As another example, component 34 may be placed in chamber 32 as device 20 is assembled, prior to inserting portion 23 of housing 22 into portion 25.

Figures 6, 7:
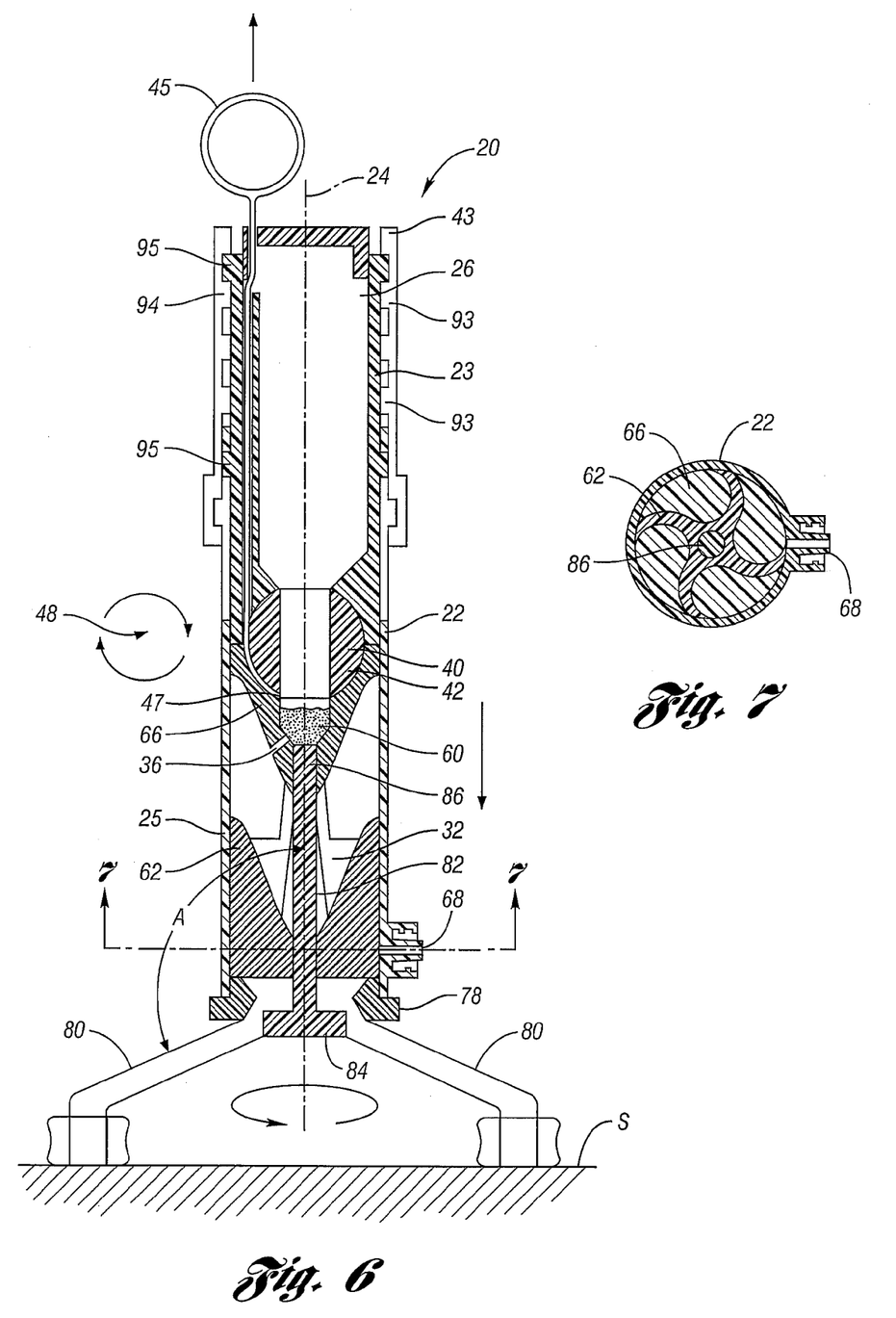
FIG. 6 is a cross sectional side view of an apparatus for stabilizing a collapsed vertebra in accordance with yet another embodiment of the present disclosure.
FIG. 7 is a sectional view 7-7 of the apparatus depicted in FIG. 6.

As seen in the example of FIG. 6, an ampoule breaking device 40 is disposed within or beneath the first chamber 26. The ampoule breaking device 40 is configured to engage the ampoule 28 and to break the ampoule 28. When the ampoule 28 is broken, the first bone cement component 30 is released into the first chamber 26 and may drain, for example by force of gravity, through the port 36 and into the second chamber 32.

Figure 12:
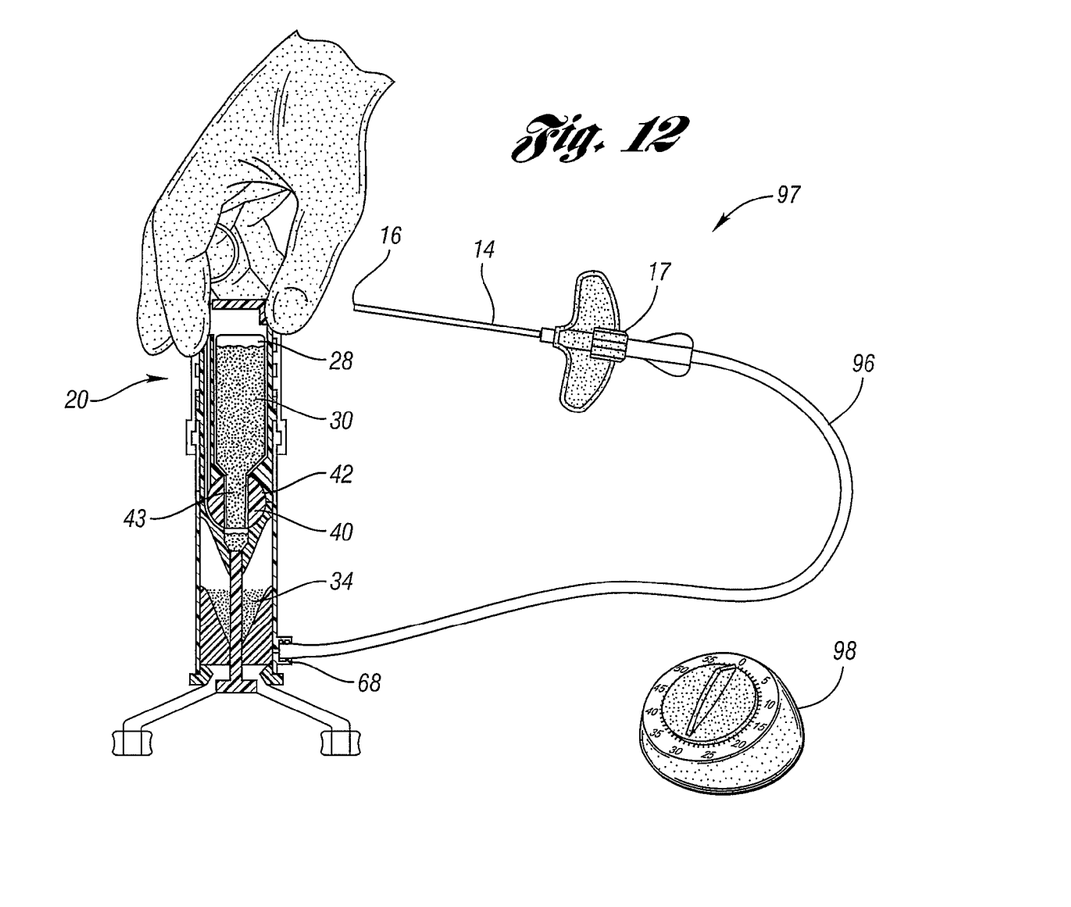
FIG. 12 is a side view of a bone cement substitute kit in accordance with one embodiment of the present disclosure.

In one example, the ampoule breaking device 40 includes a rotating member 42 disposed within the first chamber 26. As illustrated in FIG. 12, the rotating member 42 engages the ampoule 28, for example, about the head 43 of the ampoule 28. In the illustrated embodiment, member 42 has a central lumen in which head 43 or other part of ampoule 28 can fit while the remainder of ampoule 28 is in chamber 26. The rotating member 42 rotates about a transverse axis 48 (illustrated to the side in FIG. 6), which is preferably perpendicular to the longitudinal axis 24. It will therefore be seen that this example of member 42 is cylindrical or spherical, to permit easy rotation about axis 48. When the rotating member 42 rotates, it breaks the ampoule 28 into pieces by applying a rotational force about the engaged head 43, while the rest of ampoule 28 is braced against a wall of chamber 26.

The ampoule breaking device 40 may further include a cord member 44 having a first end 45 for actuation by an interventionalist and a second end 47 operably connected to the rotating member 42 to rotate the rotating member 42 during actuation of the first end 45. Cord member 44 extends through a small hole in cap 31, as seen in one example in FIG. 6. The second end 47 of the cord member 44 may be wrapped about the rotating member 42 to enable rotation of the rotating member 42 from between about 0 to 180 degrees. For example, cord member 44 may extend 180 degrees, 270 degrees or more around rotating member 42, with cord member 44 attached to the side of the lumen through rotating member 42, or being split and attached around both sides of the lumen through rotating member 42, in some embodiments. Preferably, a 180 degree rotation of the rotating member 42 spills out any remaining first bone cement component 30 that might be contained within the broken head 43 of the ampoule 28. The rotating member 42, acting as a valve, may then be turned an additional 90 degrees to a closed position (e.g. with the lumen of member 42 substantially perpendicular to axis 24 or at least with its upper opening (as seen in FIG. 6) covered, as by a portion of upper portion 23 of housing 22) to "close-off" fluid communication between the first and second chambers 26 and 32.

Figures 10A, 10B, 10C:
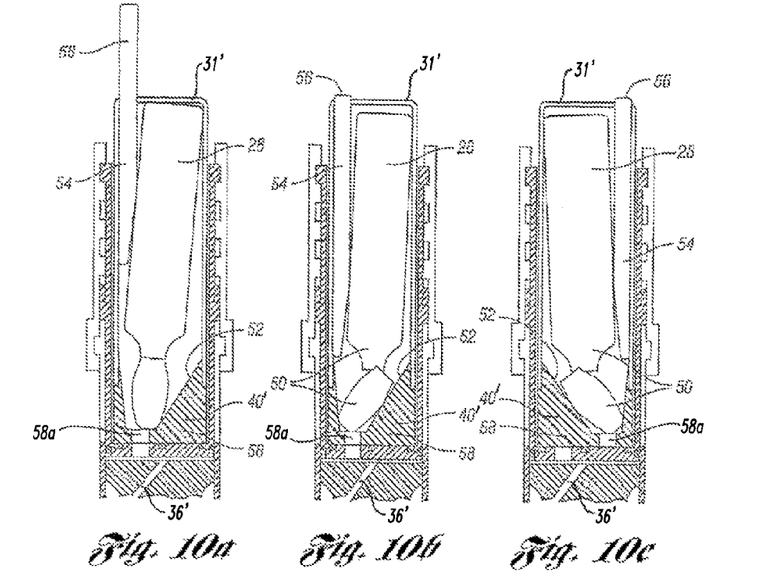
FIG. 10a is a side sectional view of an ampoule breaking device in accordance with at least one embodiment of the present disclosure.
FIG. 10b is a side sectional view of an ampoule breaking device in accordance with at least one embodiment of the present disclosure.
FIG. 10c is a side sectional view of an ampoule breaking device in accordance with at least one embodiment of the present disclosure.

Referring to FIGS. 10a-10c, an alternative embodiment for the ampoule breaking device 40' is provided. The ampoule breaking device 40' may have a surface 52 formed at an incline to the longitudinal axis 24. The ampoule breaking device 40' may include a wedge member 54 disposed within the first chamber 26 and a manually-activated control element 56 communicating with the wedge member 54 so as to move the wedge member 54 which is engaged with the ampoule 28. Control element 56 extends through a hole in a cap 31' so that it is accessible while wedge member 54 is adjacent ampoule 28. Cap 31', like cap 31, covers chamber 26 so as to prevent or limit escape of fumes from chamber 26. The wedge member 54 moves the ampoule 28 against the inclined surface 52, breaking the ampoule 28 into pieces 50, when the manually-activated control element 56 is actuated.

The ampoule breaking device 40' may further include a rotary valve portion 58, which may be rotated by the interventionist to a closed position (shown in FIG. 10c) which closes-off fluid communication between the first and second chambers 26 and 32. However, when the valve 58 is in an open position (shown in FIGS. 10a-10b), the first and second chambers 26 and 32 are in fluid communication with each other. In the illustrated example, valve 58 has an opening 58a that communicates with a port 36' leading to second chamber 32 for fluid communication (as in FIG. 10a), and when valve 58 is twisted so that opening 58a does not communicate with port 36' (e.g. FIG. 10c) fluid communication is shut off.

Referring back to FIGS. 6-9b, an impeller 62 is disposed within the second chamber 32. The impeller 62 is configured to rotate about the longitudinal axis 24 such that the impeller 62 mixes the first and second bone cement components 30 and 34 together to form the bone cement mixture 18. In one example, a vacuum tap may be provided (not shown), or the outlet 68 may be used, to de-gas the bone cement mixture 18 using the "utility" vacuum found at many healthcare facilities so as to minimize porosity and voids in the bone cement mixture 18 and to remove fumes generated by the mixture 18. Moreover, in at least one embodiment, the valve (e.g. valve 58 or breaking device 40) is in a closed position during mixing of the first and second bone cement components 30 and 34 to prevent the mixture 18 from being advanced from the second chamber 32 to the first chamber 26.

A displacer 66 is disposed adjacent to the impeller 62. The displacer 66 is configured to advance through the second chamber 32, receiving the impeller 62 and advancing the bone cement mixture 18 from the second chamber 32 through an outlet 68 which is in fluid communication with the second chamber 32. The bone cement mixture 18 is dispensed from the apparatus 20 when it is advanced through the outlet 68 by the pushing action of displacer 66.

In one example, the impeller 62 includes a plurality of blades 70. Blades 70, in the illustrated embodiments, curve outward from the middle of impeller 62. Each blade has a roughly part-cylindrical concave surface on one side and a roughly part-cylindrical convex surface on the other side. The concave surface of one blade 70 curves smoothly into the convex surface of an adjacent blade 70. Blades 70 engage the inside of housing 22 in the embodiment of FIG. 7, although it will be appreciated that other embodiments may have one or more blades 70 ending short of the housing 22. The embodiment of impeller 62 shown in FIGS. 7 and 9 has four blades 70, in pairs that generally diametrically oppose each other. Such pairs form generally an S-shape, and the pairs are generally perpendicular to each other in that embodiment. A central opening is provided in impeller 62 to accommodate shaft 86, as further discussed below.

The displacer 66 is configured to rotate about the longitudinal axis 24 and has a plurality of slots 72 formed therein which correspond with the blades 70. Each of the blades 70 have a first portion 74 and a second portion 76 extending beyond the first portion 74. The first portion 74 is disposed within a corresponding slot 72 to engage the impeller 62 such that the impeller and displacer rotate cooperatively about the longitudinal axis during mixing of the bone cement components 30 and 34. In this embodiment, impeller 62 and displacer 66 are always keyed together, that is, at no time do blades 70 entirely leave a corresponding slot 72. During dispensing of the bone cement mixture 18 from the apparatus 20, the slots 72 receive the second portions 76 of the impeller 62 as the displacer 66 advances through the second chamber 32.

The keyed relationship between displacer 66 and impeller 62 (with one or more parts of blades 70 within slots 72) results in rotation of displacer 66 with impeller 62 as impeller 62 is turned, as further discussed below. It will be seen from FIGS. 7 and 9 that in a particular embodiment slots 72 and blades 70 have a very close tolerance (e.g. little or no space between their respective side surfaces), so as to keep the mixed cement or components of it from getting between impeller 62 and displacer 66 to the extent possible, preserving as much of the cement as possible for dispensing through outlet 68.

Figure 8:
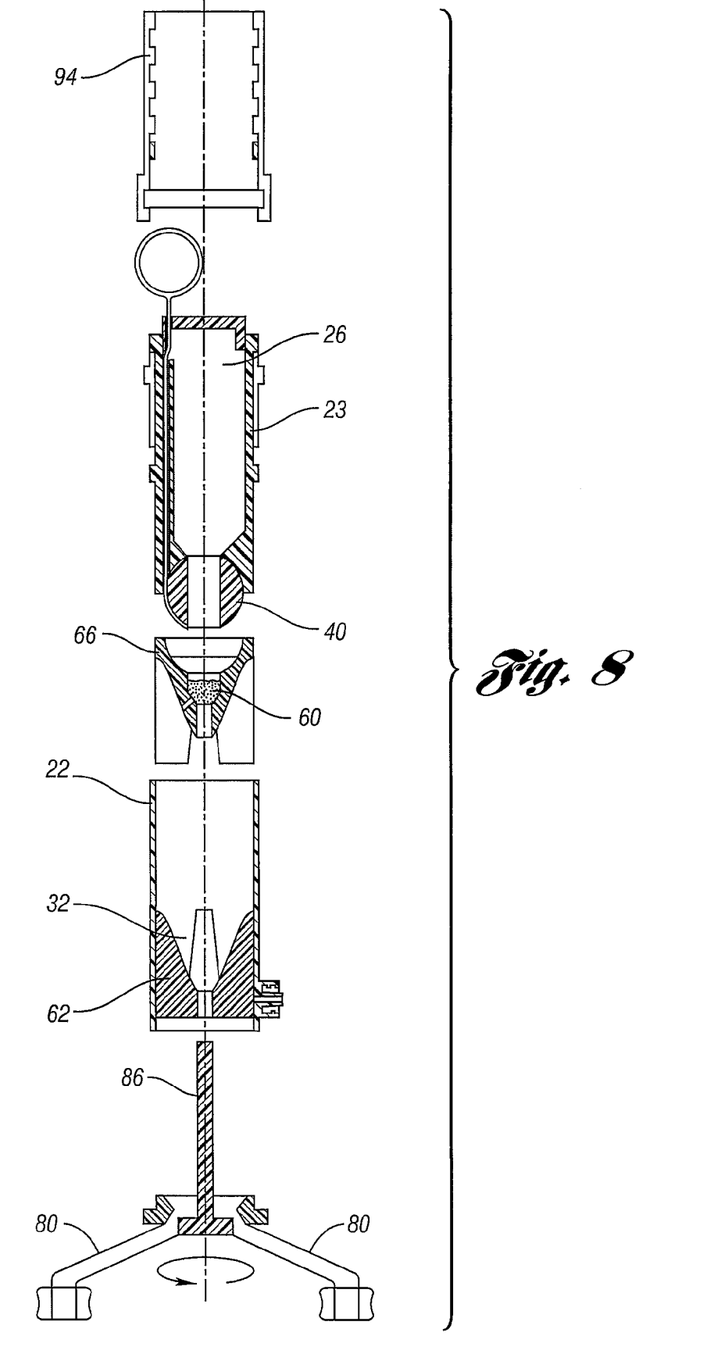
FIG. 8 is an exploded view of the apparatus depicted in FIG. 6.
Figure 9A:
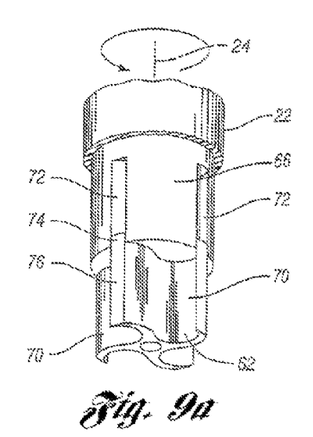
FIG. 9a is a perspective view of the displacer and impeller in a mixing configuration of the apparatus depicted in FIG. 6.
Figure 9B:
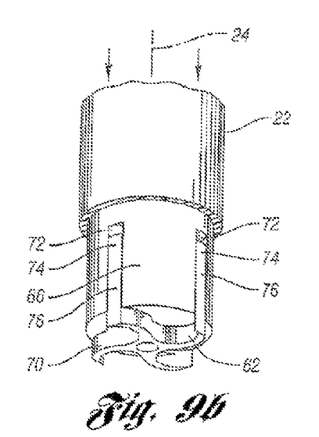
FIG. 9b is a displacer and an impeller in an advancing configuration of the apparatus depicted in FIG. 6.
Figure 9C:
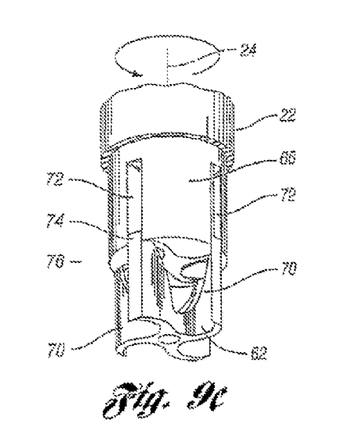
FIG. 9c is a displacer and an impeller in a mixing configuration of the apparatus depicted in FIG. 6.

FIGS. 7 and 9 demonstrate embodiments of blades 70 which are substantially parallel to axis 24 (vertical in the context of FIG. 6) from top portion 74 through portion 76 to the bottom of the blade and without holes or openings. The tips (adjacent housing 22) of blades 70 are not curved outward from the rest of the blade, as in a plowshare, in this embodiment. In other embodiments, such outward curves in a direction generally perpendicular or oblique to the remainder of blades 70 are in the tips (upper or lower) of one or more blades 70, and/or one or more openings or holes can be provided in one or more blades 70. The embodiment of FIGS. 9a and 9b also show blades that have a substantially uniform height at all points from the middle of impeller 62 out to the tips of blades 70. The cross-section of FIGS. 6 and 8, further shown in FIG. 9c, indicates an embodiment that has blades 70 with a maximum height at the tips, with the height decreasing to a minimum adjacent the opening for shaft 86 in impeller 62, with the edges of one or more blades 70 describing a curve in cross-section which may have a substantially linear portion between the minimum height and the maximum height. The curve and changing height of such blades 70 provide a central space that enhances cross-communication of the cement or its components. Displacer 66 may have slots 72 of uniform height complementary to blades 70, as seen in FIGS. 9a and 9b, or may have slots of varying height complementary to blades 70, as seen in cross-section in FIGS. 6 and 8. The illustrated embodiment of device 20 shows impeller 62 and displacer 66 remaining in their keyed relationship, i.e., blades 70 cannot be removed from slots 70 in operation of device 20. It will be appreciated that the uniform-height slots 72 of FIGS. 9a and 9b can be used with the varying-height blades 70 of FIG. 6.

A filter 60 may be disposed on the displacer 66 having the port 36 formed therethrough to provide fluid communication between the first and second chambers 26 and 32. When the ampoule 28 is broken, pieces 50 of the ampoule 28 may be received or blocked by the filter 60 while allowing the first bone cement component 30 to advance from the first chamber 26 into the second chamber 32 via the port 36. Filter 60 is shown in FIGS. 6 and 8, and it will be seen that a filter 60 may be placed over opening 58a and/or port 36' in FIGS. 10a-10c.

The apparatus 20 may further comprise a base portion 78 proximate the second chamber 32. A plurality of crank arms 80 may extend outwardly from the base portion 78. A shaft 82 has a first end 84 coupled to the crank arms 80. End 84 is slidably coupled to arms 80 in one embodiment, with end 84 having a series of splines, cogs or teeth (not shown) engaging complementary structures on one or more of arms 80. The shaft has a second end 86, which may be coupled to the displacer 66, or to the impeller 62, or both, as seen in FIG. 6. In the illustrated embodiment, end 86 is securely coupled to displacer 66 by welding, adhesives or other methods, to receive rotational motion, while impeller 62 is not joined to shaft 82 but has a seal (not shown) between impeller 62 and shaft 82 to allow shaft 82 to move longitudinally through impeller 62 without losing a significant amount of cement through impeller 62. In one example, the crank arms 80 and the shaft 82 rotate about the longitudinal axis 24, when the crank arms 80 are actuated by an interventionalist. Actuation of the crank arms 80 produces a rotational driving force which is transferred by the shaft 82 to displacer 66, if the second end 86 is coupled thereto. Alternatively, if the second end 86 is coupled to the impeller 62, the shaft 82 will transfer the rotation driving force to the impeller 62. The embodiments shown herein have impeller 62 and displacer 66 keyed together via the insertion of at least part of one or more blades 70 into one or more slots 72, and in those embodiments impeller 62 and displacer 66 will rotate together regardless of which of them (or both) is coupled to shaft end 86.

In one embodiment, there are at least three crank arms 80 positioned at an obtuse angle A of between 90 and 180 degrees from the longitudinal axis. The crank arms 80 are also spaced apart from each other such that the crank arms 80 form a stand to be supportable on a surface S and to position the apparatus 20 substantially upright.

In at least one embodiment, the housing 22 has a first portion 23 having the first chamber 26 formed therein and a second portion 25 having the second chamber 32 formed therein. The first portion 23, acting as a slide, moves relative to the second portion 25 along the longitudinal axis 24. The first portion 23 slidingly engages the displacer 66.

The apparatus 20 may further comprise a handle 94 disposed about the first portion 23. The handle 94 and the first portion 23 each have at least one flange 93 and 95 in the illustrated embodiment. The flanges 93 and 95 may be defined by grooves and/or threads formed respectively in the handle 94 and the first portion 23. This embodiment of handle 94 includes a groove 96a that fits around a boss or flange 96b of housing 22, so that handle 94 can rotate around housing 22 but not move longitudinally along housing 22. When the handle 93 is actuated, for example by rotating it about the first portion 23, the flange 93 of the handle 94 cooperates with the flange 95 of the first portion 23 to advance the first portion 23 towards the displacer 66 and sliding both within portion 25 of housing 22, such that the displacer 66 is advanced in the second chamber 32. In embodiments in which shaft 82 is securely coupled to displacer 66 and is longitudinally slidable through impeller 62, the advancing of displacer 66 causes shaft 82 to move through impeller 62. In a particular embodiment, the distance between a surface on which arms 80 rest and the lowermost point of end 84 of shaft 82 is at least approximately the same as the distance displacer 66 can travel with respect to impeller 62. In that case, when displacer 66 is moved as far as it can with respect to impeller 62 and thus forces as much cement as it can out of outlet 68, end 84 of shaft 82 will reach a surface on which arms 80 rest, providing an additional stop and support which provides an external indication of full dispensing, and can prevent significant damage to device 20 from over-tightening of handle 94.

Device 20 may be provided initially complete with second cement component 34 (for example, powdered or dry PMMA) in chamber 32 and ampoule 28 (with first cement component 30, such as liquid MMA, inside) in chamber 26, so that no transfer of components by the interventionalist or other person into device 20 is required. In other embodiments, a measure of powdered cement component may be placed in chamber 32 by the interventionalist or other person, and then displacer 66, housing portion 23, handle 94 and other parts of device 20 may be assembled. Similarly, in other embodiments ampoule 28 may be provided separately from device 20, and at the appropriate time be placed in chamber 26 and enclosed therein by cap 31, 31'.

Device 20 may be placed on a table or other suitable surface, supported by arms 80. As discussed above, ampoule 28 is broken and cement component 30 exits ampoule 28 and through port 36, 36' to chamber 32, where it encounters cement component 34. With the components together, housing 22 is grasped with one hand, as by picking it up, and arms 80 are turned with the other hand. As noted previously, turning arms 80 results in turning impeller 62, by way of the couplings between shaft 82 and arms 80 and between shaft 82 and displacer 66, and due to the keyed relationship between displacer 66 and impeller 62. The rotation of impeller 62 mixes the cement with cross-communication of the cement and/or components among the areas bounded by blades 70.

When the cement has been mixed sufficiently, device 20 can be placed again on a surface on arms 80. Turning handle 94 with respect to housing portion 22 results in a force pushing housing portion 23 downward (toward arms 80), which force is transmitted to displacer 66. Displacer 66 travels down over impeller 62, as described above, and forces cement in chamber 32 out through outlet 68.

Referring to FIG. 12, at least one embodiment of a bone cement substitute kit is provided. The kit 97 includes the apparatus 20 as discussed in the foregoing paragraphs as well as a needle 14. The needle 14 is in fluid communication with the apparatus 20 and is for advancing the bone cement mixture 18 into the collapsed vertebra 12. The needle 14 may have a beveled end 16 for easy insertion and removal from the collapsed vertebra 12. The other end 17 of the needle may be directly coupled to the apparatus 20, preferably with the outlet 68, or indirectly coupled via tubing 96. The tubing 96 provides fluid communication between the apparatus 20 and the needle 14. Preferably, the tubing 96 may have an elbow to enable the interventionalist to operate the apparatus 20 from outside an X-ray field during injection of the bone cement mixture 18 into the damaged bone. Moreover, the tubing may be pressure sensitive, indicating when the collapsed vertebra 12 is filled with the bone cement mixture 18 by changing color caused from an increase in back-pressure from the bone cement mixture 18.

The kit 97 may further comprise a first and a second bone cement component 30 and 34. The first bone cement component 30 is preferably contained within the ampoule 28, which is preferably contained within the first chamber 26 of the apparatus 20. The second bone cement component 34 is preferably contained within the second chamber 32, and may be placed there as discussed above. In one example the first bone cement component 30 is MMA and the second bone cement component 34 is PMMA.

The kit 97 may further include a balloon 100 and a timer 98. The balloon 100 is for positioning within the vertebra 12, for example, via the needle 14, a catheter or mandrel. The balloon 100 may be filled with the bone cement mixture and sealed to stabilize the collapsed vertebra 12. The timer may be used to time mixing and/or curing of the bone cement mixture 18.

Figure 13:
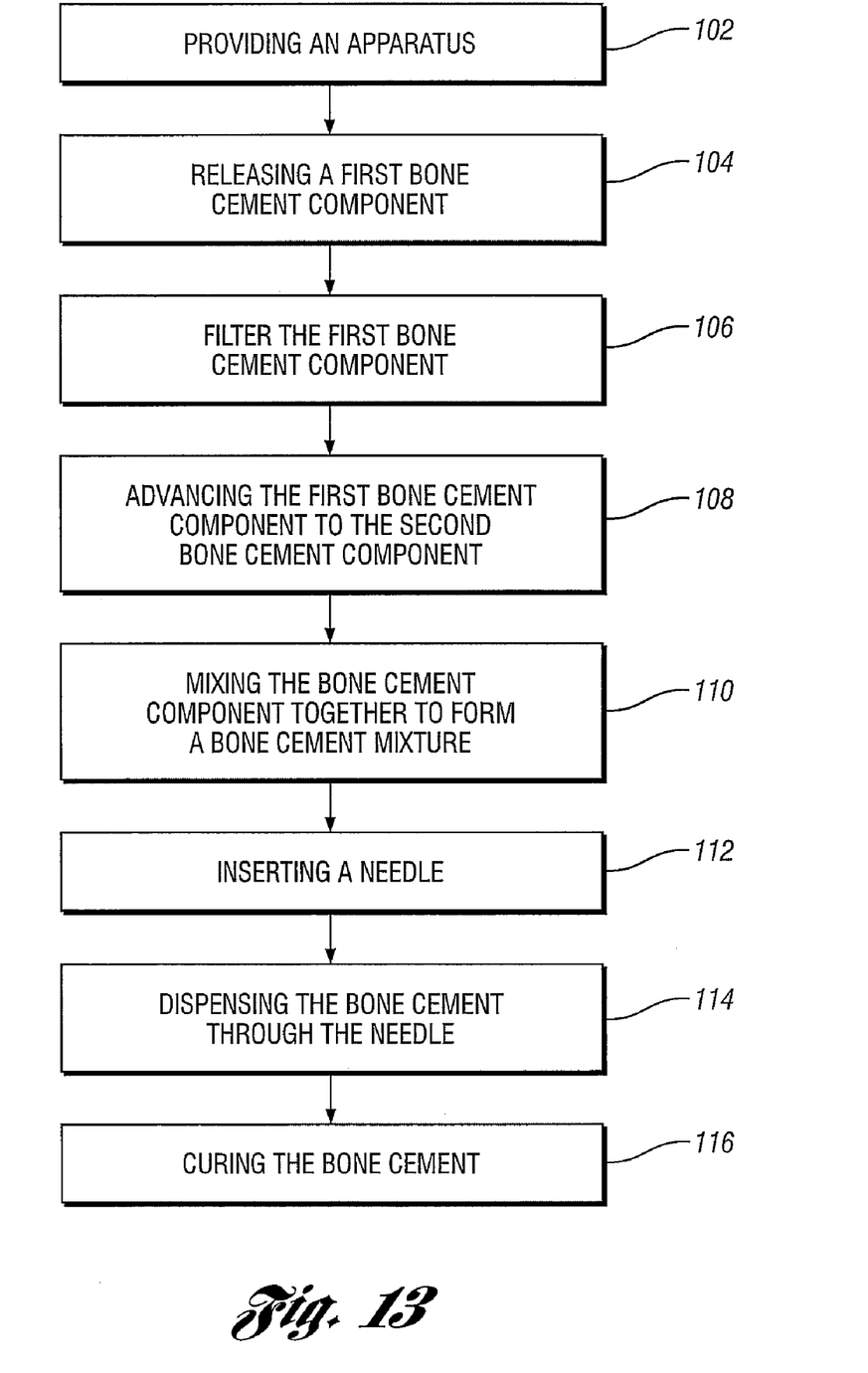
FIG. 13 is a flow chart for a method for stabilizing a damaged bone of a patient in accordance with an embodiment of the present disclosure.

Referring to FIG. 13, a method for mixing a bone cement mixture and dispensing the bone cement mixture into a damaged bone of a patient is provided. The method includes providing an apparatus (block 102), as discussed in the foregoing paragraphs.

A first bone cement component is released (block 104) from an ampoule into a first chamber. This may include breaking the ampoule within the first chamber with an ampoule breaking device as discussed above.

The first bone cement component may be filtered (block 106) by a filter in fluid communication with the first and second chambers. Pieces from the broken ampoule are received or blocked by the filter.

The first bone cement component is advanced from the first chamber into to the second chamber (block 108). The second chamber contains a second bone cement component. In one aspect, a valve may then be closed such that fluid communication between the first and second chambers is closed-off.

The first and second bone cement components are mixed together (block 110) to form a bone cement mixture. This may include rotating an impeller about a longitudinal axis to mix the bone cement components as discussed above.

A needle is inserted (block 112) into the damaged bone of the patient. The needle is in fluid communication with the apparatus.

The bone cement mixture is dispensed from the apparatus into the damaged bone of the patient via the needle (block 114). This can include advancing a displacer through the second chamber of the apparatus, where the displacer receives the impeller and advances the bone cement mixture from the second chamber and through the needle as discussed above. The bone cement mixture is then allowed to cure (block 116) to stabilize the damaged bone of a patient.

As a person skilled in the art will readily appreciate, the above description is meant as an illustration of the implementation of the principles of this disclosure. This description is not intended to limit the scope or application of this disclosure in that the disclosure is susceptible to modification variation and change, without departing from the spirit of this disclosure, as defined in the following claims.

The invention claimed is:

1. An apparatus for mixing and dispensing a bone cement mixture, the apparatus comprising:
    a housing having a longitudinal axis and a first chamber formed therein for containing an ampoule having a first bone cement component, the housing having a second chamber formed therein for containing a second bone cement component, the second chamber being in fluid communication with the first chamber, the housing including an outlet in fluid communication with the second chamber for dispensing the bone cement mixture from the apparatus;
    an ampoule breaking device disposed within the first chamber and configured to engage the ampoule to break the ampoule for release of the first bone cement component into the first chamber;
    an impeller disposed within the second chamber and being configured to rotate about the longitudinal axis such that the impeller mixes the first and second bone cement components together to form the bone cement mixture; and
    a displacer disposed adjacent the impeller and being configured to advance through the second chamber, receiving the impeller and advance the bone cement mixture from the second chamber through the outlet.

2. The apparatus according to claim 1 further comprising a filter disposed on the displacer having a port formed therethrough to provide fluid communication between the first and second chambers, the filter being configured to receive pieces of the ampoule when the ampoule is broken by the ampoule breaking device while allowing the first bone cement component to advance from the first chamber into the second chamber via the port.

3. The apparatus according to claim 1 wherein the impeller includes a plurality of blades and wherein the displacer is configured to rotate about the longitudinal axis and has a plurality of slots formed therein corresponding with the blades, each of the blades having first portions and second portions extending beyond the first portions, the first portion configured to be disposed within one of the slots to engage the impeller such that the displacer and the impeller cooperatively rotate about the longitudinal axis, and the slots receiving the second portions when the displacer is advanced through the second chamber.

4. The apparatus according to claim 1 wherein the housing has a first portion having the first chamber formed therein and a second portion having the second chamber formed therein, the first portion being configured to move relative to the second portion along the longitudinal axis and slidingly engaging the displacer, and wherein the apparatus further comprises a handle disposed about the first portion, the handle and the first portion each having at least one flange, the flange of the handle engaging the flange of the first portion, the handle being configured to be actuated, cooperating the flange of the handle with the flange of the first portion to advance the first portion towards the displacer such that the displacer is advanced in the second chamber.

5. The apparatus according to claim 1 wherein the ampoule breaking device includes a rotating member disposed within the first chamber and being configured to engage a portion of the ampoule and to rotate about a transverse axis to break the ampoule.

6. The apparatus according to claim 1 wherein the ampoule breaking device has a surface formed at an incline to the longitudinal axis and the ampoule breaking device includes a wedged member disposed within the first chamber and a manually-activated element communicating with the wedge member such that the wedge member moves the ampoule against the inclined surface when the manually-activated element is actuated, breaking the ampoule.

7. The apparatus according to claim 1 further comprising a valve disposed between the first and second chambers and being configured to be selectively actuated between an open position and a closed position such that when the valve is in the open position there is fluid communication between the first and second chamber and when the valve is in the closed position fluid communication between the first and second chambers is closed-off.

8. An apparatus for mixing and dispensing a bone cement mixture, the apparatus comprising:
    a housing having a longitudinal axis and a first chamber formed therein for containing an ampoule having a first bone cement component, the housing having a second chamber formed therein for containing a second bone cement component, the second chamber being in fluid communication with the first chamber, the housing including an outlet in fluid communication with the second chamber for dispensing the bone cement mixture from the apparatus;
    an ampoule breaking device disposed within the first chamber and configured to engage the ampoule to break the ampoule for release of the first bone cement component into the first chamber;
    an impeller disposed within the second chamber and being configured to rotate about the longitudinal axis such that the impeller mixes the first and second bone cement components together to form the bone cement mixture;
    a displacer disposed adjacent the impeller and being configured to advance through the second chamber, receiving the impeller and advance the bone cement mixture from the second chamber through the outlet; and
    a base portion proximate the second chamber, a plurality of crank arms extending outwardly from the base portion and a shaft having a first end and a second end, the first end coupled to the crank arms and the second end coupled to one of the displacer and the impeller, the crank arms configured to produce rotational driving force when actuated and the shaft transferring rotational driving force from the crank arms to the one of the displacer and the impeller.

9. The apparatus according to claim 8 wherein the plurality of crank arms includes at least three crank arms positioned at obtuse angles from the longitudinal axis such that the crank arms are supportable on a surface so as to position the apparatus substantially upright.

10. A bone cement substitute kit for mixing a bone cement and dispensing the bone cement mixture into a damaged bone of a patient, the kit comprising: an ampoule having a first bone cement component;
a second bone cement component;
an apparatus including:
a housing having a longitudinal axis and a first chamber formed therein, the first chamber for containing the ampoule, the housing having a second chamber formed therein for containing the second bone cement component, the second chamber being in fluid communication with the first chamber, the housing including an outlet in fluid communication with the second chamber for dispensing the bone cement mixture from the apparatus;
an ampoule breaking device disposed within the first chamber and configured to engage the ampoule to break the ampoule for release of the first bone cement component into the first chamber;
an impeller disposed within the second chamber and being configured to rotate about the longitudinal axis such that the impeller mixes the first and second bone cement components together to form the bone cement mixture; and
a displacer disposed adjacent the impeller and being configured to advance through the second chamber, receiving the impeller and advance the bone cement mixture from the second chamber through the outlet; and
a needle in fluid communication with the outlet and configured for receiving the bone cement mixture from the apparatus and for advancing the bone cement mixture into the damaged bone of the patient.

11. The kit according to claim 10 further comprising a timer for timing curing of the bone cement mixture.

12. The kit according to claim 10 further comprising a tubing configured to couple to both the apparatus and the needle and to provide fluid communication between the apparatus and the needle.

13. The kit according to claim 10 further comprising a balloon configured for positioning within the damaged bone of the patient and for receiving the bone cement mixture from the needle.

14. The kit according to claim 10 wherein the impeller includes a plurality of blades and wherein the displacer is configured to rotate about the longitudinal axis and has a plurality of slots formed therein corresponding with the blades, each of the blades having first portions and second portions extending beyond the first portions, the first portion configured to be disposed within one of the slots to engage the impeller such that the displacer and the impeller cooperatively rotate about the longitudinal axis, and the slots receiving the second portions when the displacer is advanced through the second chamber.

15. The kit according to claim 10 wherein the housing has a first portion having the first chamber formed therein and a second portion having the second chamber formed therein, the first portion being configured to move relative to the second portion along the longitudinal axis and slidingly engaging the displacer, and wherein the apparatus further comprises a handle disposed about the first portion, the handle and the first portion each having at least one flange, the flange of the handle engaging the flange of the first portion, the handle being configured to be actuated, cooperating the flange of the handle with the flange of the first portion to advance the first portion towards the displacer such that the displacer is advanced in the second chamber.

16. The kit according to claim 10 wherein the ampoule breaking device has a surface formed at an incline to the longitudinal axis and the ampoule breaking device includes a wedged member disposed within the first chamber and a manually-activated element communicating with the wedge member such that the wedge member moves the ampoule against the inclined surface when the manually-activated element is actuated, breaking the ampoule.

17. A bone cement substitute kit for mixing a bone cement and dispensing the bone cement mixture into a damaged bone of a patient, the kit comprising: an ampoule having a first bone cement component;
a second bone cement component;
an apparatus including:
a housing having a longitudinal axis and a first chamber formed therein, the first chamber for containing the ampoule, the housing having a second chamber formed therein for containing the second bone cement component, the second chamber being in fluid communication with the first chamber, the housing including an outlet in fluid communication with the second chamber for dispensing the bone cement mixture from the apparatus;
an ampoule breaking device disposed within the first chamber and configured to engage the ampoule to break the ampoule for release of the first bone cement component into the first chamber;
an impeller disposed within the second chamber and being configured to rotate about the longitudinal axis such that the impeller mixes the first and second bone cement components together to form the bone cement mixture; and
a displacer disposed adjacent the impeller and being configured to advance through the second chamber, receiving the impeller and advance the bone cement mixture from the second chamber through the outlet; and
a needle in fluid communication with the outlet and configured for receiving the bone cement mixture from the apparatus and for advancing the bone cement mixture into the damaged bone of the patient,
wherein the apparatus further includes a base portion proximate the second chamber, a plurality of crank arms extending outwardly from the base portion and a shaft having a first end and a second end, the first end coupled to the crank arms and the second end coupled to one of the displacer and the impeller, the crank arms configured to produce rotational driving force when actuated and the shaft transferring rotational driving force from the crank arms to the one of the displacer and the impeller.

18. A bone cement substitute kit for mixing a bone cement and dispensing the bone cement mixture into a damaged bone of a patient, the kit comprising: an ampoule having a first bone cement component;
a second bone cement component;
an apparatus including:
a housing having a longitudinal axis and a first chamber formed therein, the first chamber for containing the ampoule, the housing having a second chamber formed therein for containing the second bone cement component, the second chamber being in fluid communication with the first chamber, the housing including an outlet in fluid communication with the second chamber for dispensing the bone cement mixture from the apparatus;

an ampoule breaking device disposed within the first chamber and configured to engage the ampoule to break the ampoule for release of the first bone cement component into the first chamber;

an impeller disposed within the second chamber and being configured to rotate about the longitudinal axis such that the impeller mixes the first and second bone cement components together to form the bone cement mixture; and a displacer disposed adjacent the impeller and being configured to advance through the second chamber, receiving the impeller and advance the bone cement mixture from the second chamber through the outlet; and a needle in fluid communication with the outlet and configured for receiving the bone cement mixture from the apparatus and for advancing the bone cement mixture into the damaged bone of the patient, wherein the ampoule breaking device includes a rotating member and a cord member, the rotating member disposed within the first chamber and being configured to engage a portion of the ampoule and to rotate about a transverse axis, the cord member having a first end for actuation and a second end operably connected to the rotating member to rotate the rotating member during actuation of the first end, breaking the ampoule.

19. An apparatus for mixing and dispensing a bone cement mixture, the apparatus comprising:

a housing having a longitudinal axis and a first chamber formed therein for containing an ampoule having a first bone cement component, the housing having a second chamber formed therein for containing a second bone cement component, the second chamber being in fluid communication with the first chamber, the housing including an outlet in fluid communication with the second chamber for dispensing the bone cement mixture from the apparatus;

an ampoule breaking device disposed within the first chamber and configured to engage the ampoule to break the ampoule for release of the first bone cement component into the first chamber;

an impeller disposed within the second chamber and being configured to rotate about the longitudinal axis such that the impeller mixes the first and second bone cement components together to form the bone cement mixture; and a displacer disposed adjacent the impeller and being configured to advance through the second chamber, receiving the impeller and advance the bone cement mixture from the second chamber through the outlet, wherein the ampoule breaking device further includes a cord member having a first end for actuation and a second end operably connected to the ampoule breaking device to rotate at least part of the ampoule breaking device during actuation of the first end, breaking the ampoule.

20. The apparatus according to claim 19, wherein the ampoule breaking device includes a rotating member disposed within the first chamber and connected to the cord, the rotating member being configured to engage a portion of the ampoule and to rotate about a transverse axis to break the ampoule.

* * * * *